United States Patent [19]

Miller et al.

[11] Patent Number: 5,322,799
[45] Date of Patent: Jun. 21, 1994

[54] OBSERVATION CELL AND MIXING CHAMBER

[75] Inventors: Robert J. Miller, Stanford, Calif.; James D. Ingle, Jr., Corvallis, Oreg.

[73] Assignee: The State of Oregon Acting by and through the State Board of Higher Education on Behalf of Oregon State University, Eugene, Oreg.

[21] Appl. No.: 733,753

[22] Filed: Jul. 23, 1991

Related U.S. Application Data

[63] Continuation-in-part of Ser. No. 152,012, Feb. 3, 1988, Pat. No. 5,034,194.

[51] Int. Cl.$^5$ ............................................ B01L 3/00
[52] U.S. Cl. .................................... 436/165; 436/164; 436/172; 436/909; 422/99; 422/102; 422/104; 422/58
[58] Field of Search ................ 422/99, 102, 104, 58, 422/55, 68; 436/164, 165, 172, 909; 356/246, 440; 250/576; 137/3, 8

[56] References Cited

U.S. PATENT DOCUMENTS

| | | | |
|---|---|---|---|
| 4,037,974 | 7/1977 | Fletcher et al. | 356/246 |
| 4,074,940 | 2/1978 | Tarbet | 356/246 |
| 4,169,078 | 9/1979 | Spicuzza, Jr. et al. | 260/17.3 |
| 4,171,913 | 10/1979 | Wildy et al. | 356/325 |
| 4,180,739 | 12/1979 | Abu-Shumays | 250/461 R |
| 4,181,853 | 1/1980 | Abu-Shumays et al. | 250/304 |
| 4,283,141 | 8/1981 | Stockdale et al. | 356/246 |
| 4,304,490 | 12/1981 | Murakoshi et al. | 356/319 |
| 4,643,570 | 2/1987 | Mächler et al. | 250/576 X |
| 4,643,580 | 2/1987 | Gross et al. | 250/576 X |
| 4,668,091 | 5/1987 | Lagesson et al. | 356/246 |
| 4,734,260 | 3/1988 | Lautenschläger | 436/165 X |
| 4,747,687 | 5/1988 | Hoppe et al. | 356/246 |
| 5,034,194 | 7/1991 | Miller et al. | 422/99 |
| 5,120,129 | 6/1992 | Farguharson et al. | 356/246 |
| 5,160,974 | 11/1992 | Siegel et al. | 356/246 |

OTHER PUBLICATIONS

Birks, J. and Kuge, M., "Chemiluminescent Aerosol Spray Detector for Liquid Chromatography," *Anal. Chem.* 52: 897-901 (1980).

Lidosfky, S., et al., "Laser Fluorescense Immunoassay of Insulin," *Anal. Chem. 51*: 1602-1605 (1979).

Diebold, J. and Zare, R., "Laser Fluorimetry: Subpicogram Detection of Aflatoxins Using High-Pressure Liquid Chromatography," *Science 196*: 1439-1441 (1977).

Hershberger, L., et al., "Sub-Microlite Flow-Through Cuvette or Fluorescence Monitoring of High Perl formance Liquid Chromatographic Effluents," *Anal. Chem.* 51: 1444-1446 (1979).

*Primary Examiner*—James C. Housel
*Assistant Examiner*—Long V. Le
*Attorney, Agent, or Firm*—Klarquist Sparkman Campbell Leigh & Whinston

[57] ABSTRACT

A device for detecting substances in a liquid film by measuring chemiluminescence, fluorescence or absorption using techniques such as flow-injection analysis schemes, liquid chromatographies, and gas chromatographies. The device can be used as a micro-volume mixing or reaction substrate for a variety of measurements. The device comprises at least two film supports that are separated by a small gap. One or more applicators are positioned along the gap to supply fluids to the gap. The applicators are positioned near the gap at a spacing that is near the necking length of the fluid supplied by the applicator. A thin, continuous film of the mixture of fluids to be examined is supported in the gap between the film supports. The film extends through the examining chamber and through drop and overflow detection probes. Also disclosed is a mixing or reaction chamber which comprises an enclosable mainframe into which a plurality of applicators are butted near a gap defined between two film supports. The chamber communicates with an inlet port and an exit port for controlling the pressure and other aspects of the environment in the chamber.

14 Claims, 4 Drawing Sheets

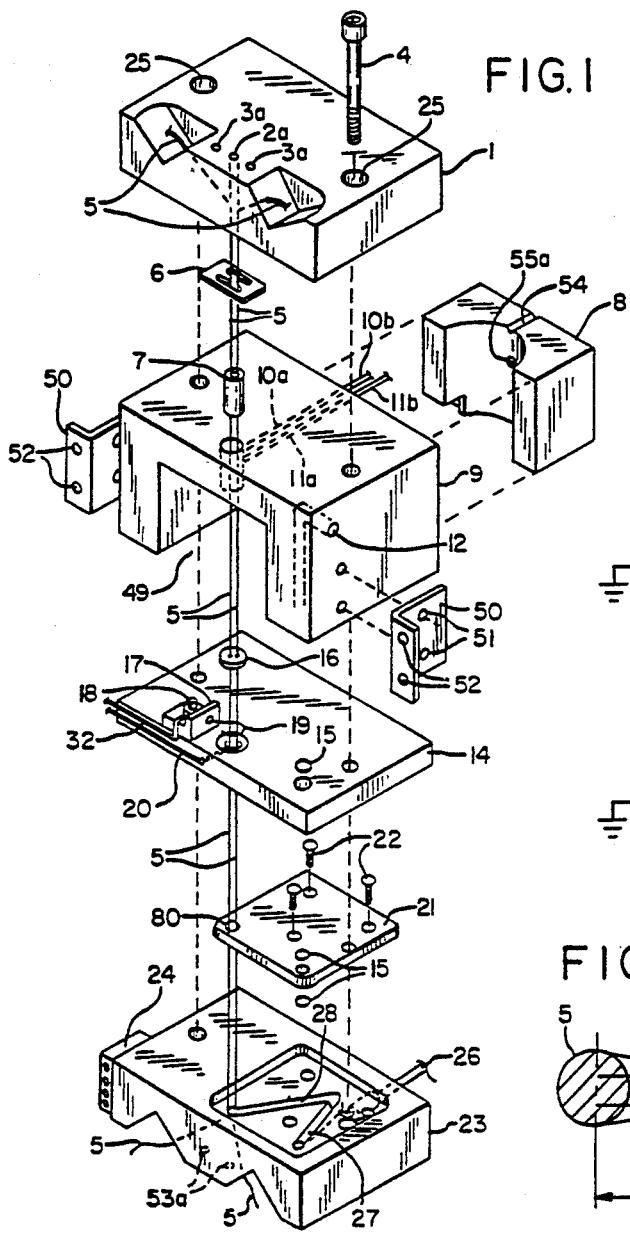
FIG.1
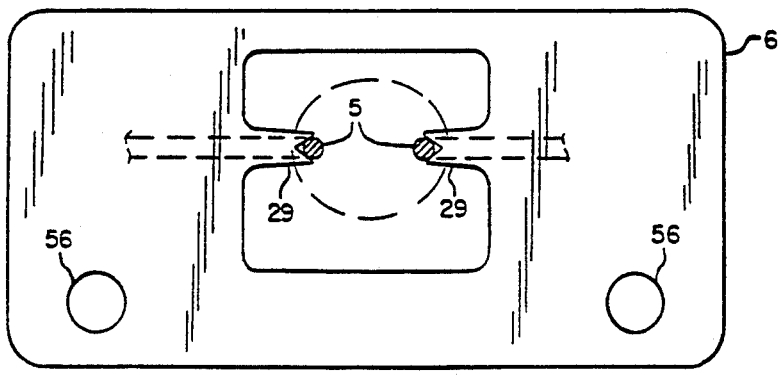
FIG.2
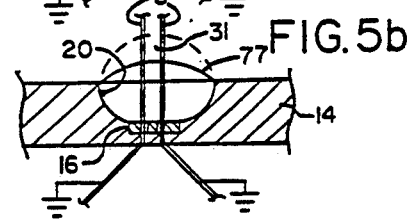
FIG.5a
FIG.5b
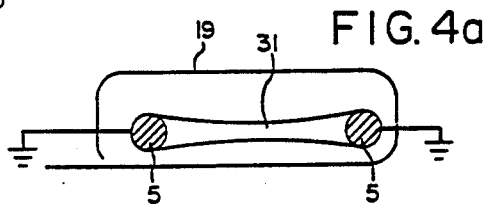
FIG.4a
FIG.4b
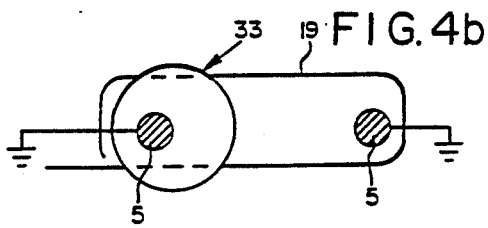
FIG.6
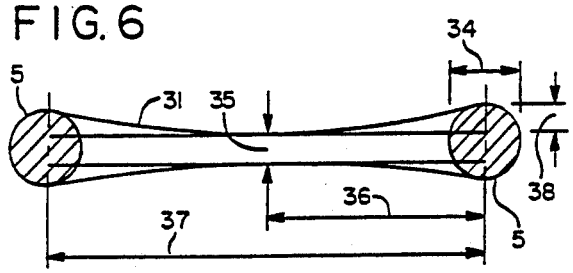
FIG.3

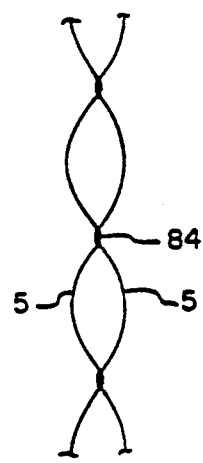
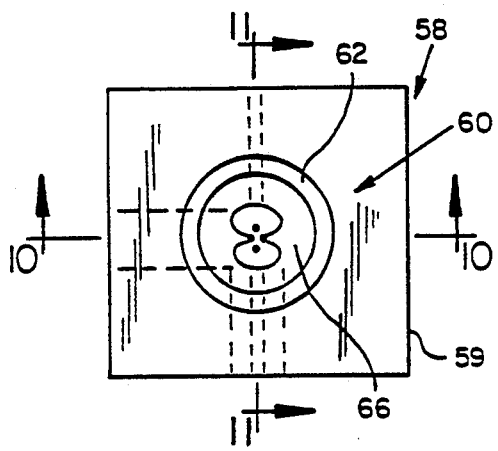
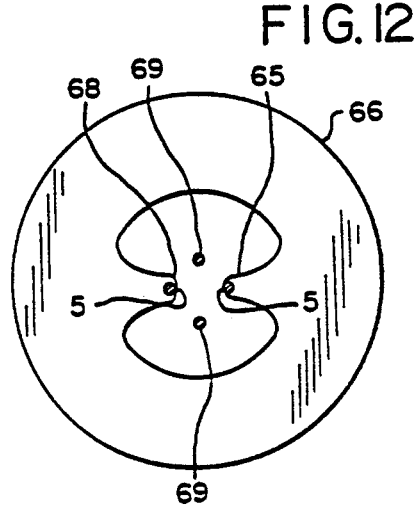
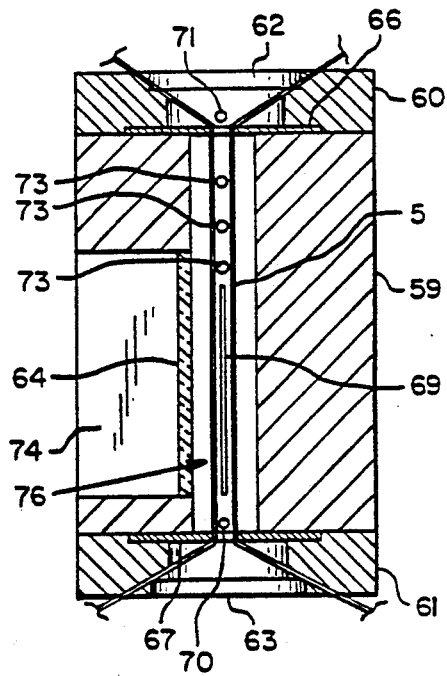
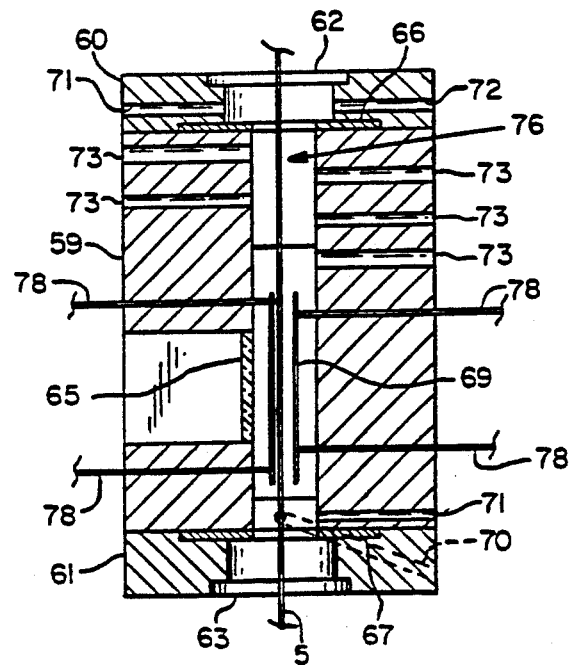

OBSERVATION CELL AND MIXING CHAMBER

This is a continuation-in-part of application Ser. No. 07/152,012, filed Feb. 3, 1988, now patent No. 5,034,194, which is incorporated herein by this reference.

This invention was made with the government support under Grant Nos. CHE 7616711 and CHE 7921247 awarded by the National Science Foundation. The government has certain rights in this invention.

BACKGROUND OF THE INVENTION

This invention relates to devices for the detection and to devices for rapid mixing of liquid substances in small volumes.

In certain analytical procedures, it is necessary or advantageous to measure properties of liquids present in small volumes. Devices for such purposes are shown in U.S. Pat. Nos. 4,643,570 (Machler, et al) and 4,643,580 (Gross, et al).

Some sample flow cells in the past have had problems with light from an excitation source. See, for example, U.S. Pat. No. 4,037,974, which provides for an opaque mask and/or specially designed sample flow cell with coating material to reduce the problem of light from an excitation source. Furthermore, sampling of small flow volume has presented some difficulties with unwanted introduction of air bubbles. See, for example, U.S. Pat. No. 4,074,940. Another problem arises in having sufficient fluorescence quantum yield for adequate detection which can be solved by a method and apparatus using a stationary phase for sampling as shown in U.S. Pat. No. 4,181,853.

Windowless flow cells by design minimize scattered light. Two previous designs for windowless spectroscopic flow cells have been reported. One design is based upon the suspension of the flowing stream between an outlet capillary tube and a small diameter rod placed directly below the outlet tube. A stationary, but constantly replenished four microliter droplet is formed in the gap between the tube and the rod. The second design is based on directing the flowing stream from a capillary tube across the gap to another capillary tube. The effluent stream is confined by sheathing with a flowing solvent to provide a windowless optical volume of 0.006 to 0.15 microliters.

SUMMARY OF THE INVENTION

It is an object of this invention to provide a liquid film observation apparatus which avoids the interaction of a probing or probed light beam with optical materials which cause undesirable effects such as reflection, scattering, absorption, and background fluorescence.

It is a further object to eliminate sorption of substances in the film onto container walls or desorption of substances from the container walls into the film.

It is another object to provide very small optical dead volumes to achieve resolution of two or more substances contained in two or more small volume elements separated in time in a flowing film.

Another object is to provide an optically thin media useful for the detection of highly absorbing substances and for minimization of undesired absorption effects in luminescence measurements.

An additional object is to provide the ability to study time resolved behavior by probing different regions of a flowing film.

These objectives are achieved by the present invention in which at least two film supports are separated by a small gap. One or more applicators are positioned along the gap. The term film support is defined for this invention as the solid-to-liquid interface that serves as the attachment point for the liquid film. An interconnecting structural member or frame holds the film supports such that there is a gap between the film supports.

Examples of suitable film supports include metallic wires, polymer filaments, and knife edges. The supports may be uncoated, e.g. consist of native metallic oxide, or may have ceramic, organic, or other coatings. The shape and composition of the supports and their spacing is selected such that a continuous liquid film can be sustained in the gap between the supports.

In a preferred embodiment, the supports are wires and each wire has a cross-sectional perimeter that is circular or rectangular. A film is established by initiating fluid flow through at least one applicator abutted near the gap between the wires. Additional applicators are properly spaced and angled alongside the gap to provide liquid that mixes with the liquid film in the gap.

The properly adjusted spacing of the abutted applicator to the gap is determined by the necking length of the liquid that exits the applicator. A spacing near the necking length is required for optimal mixing of the fluids. A spacing of near zero is desired for an alternative configuration that assures minimal mixing for observing streamline flow on the film. The applicator typically consists of a Teflon tube or a pipette tip having an inside diameter not exceeding the width of the gap between the film supports. The angle outlined by line segments representing the intersecting liquid in the applicator with the liquid film in the gap is typically 45° and 90°.

Apparatus is provided for forming a continuous film in the gap, for adjusting the spacing and angle of the supports relative to each other so as to adjust the width and shape of the gap, and for adjusting the spacing and angle between each applicator and the gap. The geometric shape and dimensions of the liquid film suspended or flowing in the gap is determined by the size of the film supports, the width of the gap and the flow rate of the liquid film.

Since the static or flowing-liquid film formed in the gap need not have exterior surfaces, no optical materials are required in the optical path of a probing or probed light beam.

In one embodiment, a flowing-liquid film moves from an applicator tube to a receiving or collection tube.

The gap width can not exceed a critical width above which a continuous liquid film does not form between the film supports.

The film supports can be selected or pre-treated to obtain desired wetting properties or chemical reactivities. The term chemically reactive is defined as a measurable enhancement or inhibition of a measured response by a detector; film supports having this behavior are termed active film supports. For example, a support which contains a detectable or reactive substance that leaches into the film is considered an active film support. Similarly, a support that bears a catalyst is an active support if it effects some detectable property of the film. Film supports without detectable effects on a measured response are termed passive film supports.

The flow cell is suitable for the detection of species directly by chemiluminescence, fluorescence or absorption based measurements such as in a flow injection analysis scheme or stopped flow technique. Versatility also allows direct interfacing to a liquid chromatograph or to the effluent from a gas chromatograph. Furthermore, the mixing characteristics of the properly designed invention suggest its use as a micro-volume mixing or reaction chamber for a variety of experiments.

In one embodiment, a Plexiglas mainframe would contain viewing windows that may or may not contain an optical material above, below and on the side of the examining chamber. Liquids exiting a plurality of reagent applicators, with properly adjusted applicator to film spacings, form a pulsing film.

Another embodiment uses two supports twisted in a helical form with nodes where the two supports are physically joined. A capillary tube is used to transfer the mixed fluid from the cell wire film supports to another location. The enclosed examining chamber also comprises an inlet and outlet for control of the pressure and other environmental conditions in the chamber.

In a preferred embodiment of the windowless flow cell and micro-volume mixing chamber, flowing film returns to a tube confined plug flow (i.e. first in, first out). The tube confined plug flow is accomplished by abutting a wettable reagent applicator tube directly against the flowing film supports. A return to plug flow is desirable when the windowless flow cell or micro-volume mixing chamber is located up-stream from any subsequent detecting or fraction collecting instrumentation.

BRIEF DESCRIPTION OF THE DRAWINGS

FIG. 1 is an exploded perspective view of a flow cell according to the present invention.

FIG. 2 is a top view of the upper spacer.

FIG. 3 is a top view of the lower spacer.

FIG. 4a is a top sectional view of the film with drop detector probes.

FIG. 4b is a top cross sectional view of a drop in contact with the drop detector probes.

FIG. 5a is a front cross sectional view of the overflow detector probes.

FIG. 5b is a front cross sectional view with liquid in contact with the overflow detector probes.

FIG. 6 is a detailed cross sectional view of the film.

FIG. 9 is a top view of the micro-volume mixing chamber.

FIG. 10 is a front cross sectional view of the mixing chamber along lines 10—10 of FIG. 9.

FIG. 11 is a cross sectional side view of the mixing chamber along lines 11—11 of FIG. 9.

FIG. 12 is a top enlarged view of the upper spacer.

FIG. 13 is a perspective view of helical cell wires.

DETAILED DESCRIPTION

Figure 7:
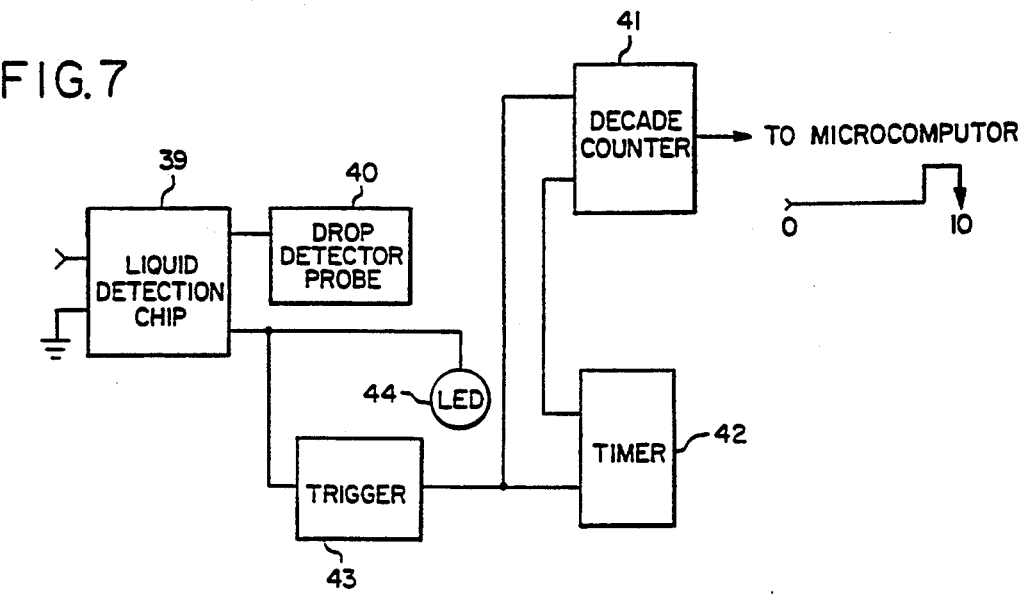
FIG. 7 is a block circuit diagram of the drop detector probe.

FIG. 1 shows an exploded view of a flow cell in a preferred embodiment which is physically constructed with an upper body plate 1, a mid-body plate 9 into which slides a mirror block 8, a lower body spacer plate 14, and a lower body plate 23. Anchor bolts 4 attach the upper body plate 1, the mid-body plate 9, the lower body spacer plate 14, and the lower body plate 23 together through anchor bolt holes 25.

Film supports 5 consisting of wire are firmly positioned in the upper body plate 1 by upper body film support set screws 3b (not shown) in the upper body set screw holes 3a. The film supports 5 are further positioned in the upper support spacer 6 before passing through the mid-body plate 9 within the Teflon insert 7. The film supports 5 continue through the examining chamber 49, the drop detector probe 19, and the overflow detector probe 20. Within the lower body spacer plate 14 is the lower support spacer 16 through which the film supports 5 pass. The film supports 5 then pass through hole 80 of the drain cavity cover 21 and the drain cavity 28 until fixed by lower body film support set screws (not shown) operating through lower body set screw holes 53a in lower body plate 23.

Fluid flow along the film supports 5 is initiated through the primary reagent port 2a by a primary reagent applicator (not shown). The applicators in the illustrated embodiment are Teflon tubes, but other materials such as glass pipettes would be suitable for some applications. Secondary reagent port 10a is located through mid-body plate 9 and through insert 7. Secondary reagent applicator 10b is positioned within secondary reagent port 10a until "near the film supports" 5. Where "near the film supports" refer to a carefully adjusted film support to applicator spacing. The distance corresponds to approximately 90% of the necking length of the emerging jet stream. When properly adjusted, the falling film will rapidly pulsate. Tertiary reagent port 11a is located within the mid-body plate 9 and directly below secondary reagent port 10a. Tertiary reagent port 11a runs through the mid-body plate 9 also penetrating Teflon insert 7. Tertiary reagent applicator 11b is positioned within tertiary reagent port 11a until "near film supports" 5. Analyte reagent port 54 is located in mirror block 8. Auxiliary port 55a is located in the center of mirror block 8 which corresponds to the geometric center of the examining chamber 49. Similarly analyte reagent applicator (not shown) and auxiliary applicator 55b (see FIG. 14) are appropriately positioned "near film supports" 5. When utilizing any port other than the primary, flow must be initiated in each of these ports prior to the introduction of a flow from the primary port. Air inlet port 12 is cut within mid-body plate 9 through the lower body spacer plate 14 with the accompanying o-rings 15 and through drain cavity cover 21 to the air inlet cavity 27. Fluid flow originating from the primary reagent applicator (not shown), the secondary reagent applicator 10b, and the tertiary reagent applicator 11b flow to the drain cavity 28 located in the lower body plate 23. Drain cavity 28 and air inlet cavity 27 join at drain port 27 to exit from the flow cell. Drain port 26 is attached to a low vacuum source (not shown).

Drain cavity cover 21 is attached to lower body plate 23 by drain cavity cover screws 22. Mounting brackets 50 are attached to mid-body plate 9 by means of bracket attachment screw holes 51.

Mounting brackets 50 can also be attached to other instruments by means of flow cell attachment screw holes 52. Cell probe block 17 is mounted to the lower body spacer plate 14 by means of mounting screw 18. Drop detector probe 19 and overflow detector probe 20 and probe wires 32 are configured around film supports 5 and lead to four wire connectors 24 for appropriate electronic attachments.

FIG. 2 is an enlargement of upper spacer 6 with spacer screw holes 56. The film supports 5 are held in place by upper spacer prongs 29. The upper body plate 1 is machined to receive upper spacer 6. Primary reagent tube 2a rests on film supports 5 close to upper spacer 6.

FIG. 3 is an enlarged view of lower spacer 16 showing two clearance holes 30 through which the film supports 5 pass.

FIG. 4a shows the film 31 held by grounded film supports 5 and encircled by drop detector probe 19.

In FIG. 4b, a drop 33 has formed so that the drop detector probe 19 will activate the circuitry shown in FIG. 7. In general, the drop 33 flows down one of the film supports 5.

FIG. 5a shows the film 31 held by grounded conductive film supports running through the lower spacer 16 located in the lower body spacer plate 14 containing the overflow detector probe 20.

Figure 8:
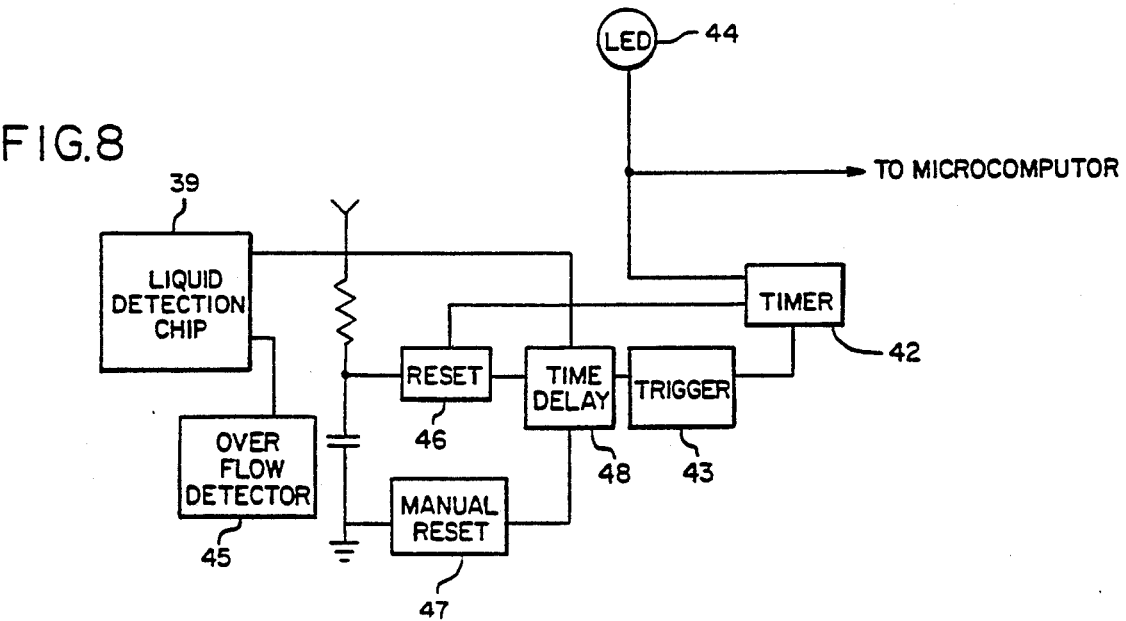
FIG. 8 is a block circuit diagram of the overflow detector probe.

In FIG. 5b, an overflow 77 has occurred resulting in the detection of an overflow condition by the overflow detector probe 20 which in turn activates the circuitry shown in FIG. 8.

FIG. 6 shows a cross section view of the film 31 between the film supports 5. The minimum film thickness 35 is shown, along with the distance between film supports 37 and one half the distance between film supports 36. The circular film support diameter 34 is shown. One half of the additional maximum film thickness 38 is shown.

FIG. 7 shows a block circuit diagram for the drop detector probe 40. A liquid detection chip 39 consisting of a LM 1830 fluid detecting IC chip, provides output to an LED 44 and a trigger chip 43 when the drop detector probe 40 to film support capacitance is shorted by a drop 33. The trigger 43 connects to a timer chip 42 and a decade counter chip 41 which in turn is connected to a microcomputer (not shown). The timer chip 42 is also connected to the decade counter chip 41.

FIG. 8 uses another similar liquid detection chip 39 with the overflow detector probe 45 which operates a time-delay circuit 48, trigger chip 43, timer chip 42, and LED 44. Automatic reset 46 is activated with the timer chip 42. The timer chip 42 is connected to a microcomputer (not shown). Also provided is a manual reset button 47.

FIG. 9 is a top view of the proposed micro-volume mixing chamber 58. The mixing chamber top 60 shows a top viewing window 62 through which the top spacer 66 can be seen. The main frame 59 is under the mixing chamber top 60. The top spacer 66 is mounted on the mixing chamber top 60.

FIG. 10 is a front cut-away view of the proposed micro-volume mixing chamber 58. The main frame 59 would have a hollow cylinder 76 through the center portion. The top 60 will attach to the main frame 59. Similarly, the bottom 61 and bottom spacer 67 will attach to the main frame 59. Top viewing window 62 and bottom viewing window 63 would allow viewing throughout the length of the hollow cylinder 76. Side viewing window 64 would allow viewing through the side viewing chamber 74. Proposed pressure regulating inlet/outlet 71 is shown within top 60. The film supports illustrated as wires 5 are shown within the hollow cylinder 76. A capillary exit port 70 is shown between film supports 5 and above bottom spacer 67. Reagent ports 73 are shown.

FIG. 11 is a side view of the proposed micro-volume mixing chamber 58. The front viewing chamber 75 with front viewing window 65 is shown cut into the main frame 59. The full length of the capillary exit port 70 is shown from the film supports 5 through the bottom 61. The pressure regulating gas inlet/outlet 71 is shown with the primary reagent port 72 within the top 60. Additional reagent ports 73 are proposed as shown. Another pressure regulating gas inlet/outlet 71 could be positioned near the bottom 61. The use as an inlet or outlet is determined by whether the gas is heavier or lighter than air. Additionally, pressure can be reduced or increased.

FIG. 12 is a detailed view of the top spacer 66. Film supports 5 would be spaced as illustrated.

FIG. 13 is another embodiment of the film supports 5 where the film supports 5 cross and are joined together at geometrically-shaped nodes 84. The geometrically-shaped nodes 84 act as an aid in mixing the reagents by a process similar to an aerodynamically-shaped wing.

Figure 14:
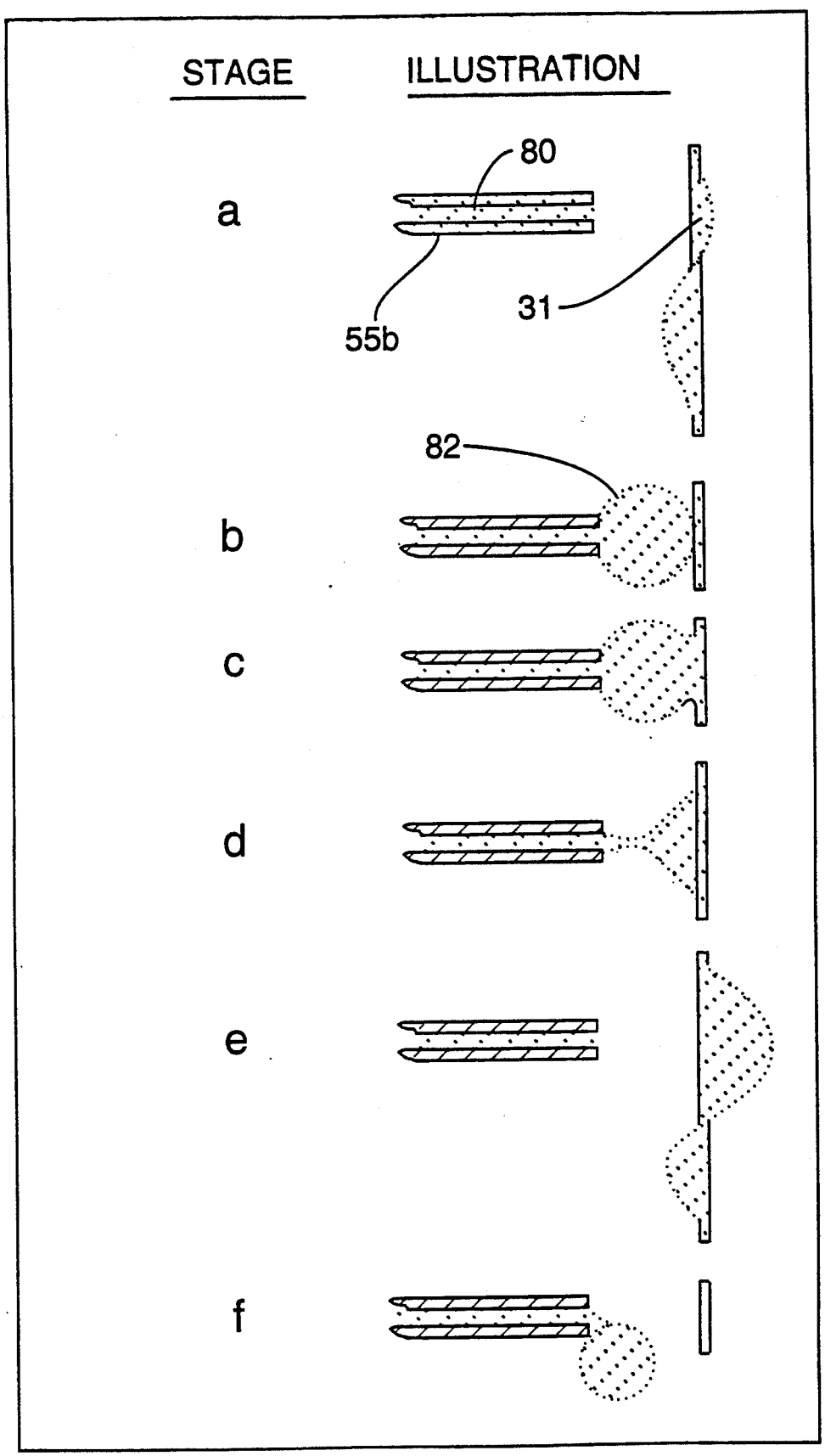
FIG. 14 is a partial, sectional view showing the transfer of liquid from an applicator to a film.

FIG. 14 shows the spacing from a reagent applicator tube to the film 31. The jet stream necking and the spacing from the end of the reagent applicator to the film 31 is about 90% of the necking distance of the emerging jet stream.

In operating the preferred embodiment as a flow cell, a reagent is provided to the primary reagent port 2a by inserting primary reagent applicator which forms a film 31 between the film supports 5. The preferred distance 37 between the film supports 5 is 1.82 millimeters. The examining chamber 49 is 2.5 cm long and the film supports are 30 gauge wires of nichrome. The film 31 will begin flowing between the two film supports 5 and through the Teflon insert 7. If a secondary reagent and/or a tertiary reagent are used, the reagents flow through the secondary reagent tube 10b and the tertiary reagent applicator 11b inserted, respectively, in the secondary reagent port 10a and the tertiary reagent port 11a through the Teflon insert 7 and finally onto the film supports 5 prior to the initiation of flow from the primary applicator through the primary reagent port 2a which form the film 31.

When operating in a flowing film mode, such as the fixed-applicator downflow mode illustrated, flow is first initiated through the downstream-most applicator. Then, each successive applicator is activated. The last applicator activated is the primary applicator which is the most upstream source of liquid for the flowing film. As an alternative, applicator flow can be started in any order if the applicators are first spaced an inoperative distance away from the gap and then moved closer until liquid from the applicators starts to enter the gap.

The film 31 flows through the examining chamber 49 and through the drop detector probe 19. The lower spacer 16 causes the film 31 to divide and flow down each film support 5 to the drain cavity 28.

Air is provided to air inlet port 12 which flows through the mid-body plate 9, o-ring 15, lower body spacer plate 14, o-ring 15, and the drain cavity cover 21 into the air inlet cavity 27. Drain port 26 is connected to a low vacuum source which then removes the air and reagent from the air inlet cavity 27 and the drain cavity 28, respectively, through the drain port 26.

The mounting brackets 50 are attached to a photomultiplier tube housing for continuous flow chemiluminescence measurements.

Referring to FIG. 4b a condition is shown where the film 31 has not formed and a drop 33 is passing through the drop detector probe 19. Referring now to FIG. 7, the liquid detection chip 39 provides an AC signal to the drop detector probe 19. When a drop 33 passes through the drop detector probes 19, the LED 44 will light. The output of the liquid detection chip 39 is debounced by a Schmidt trigger chip 34 and connected to the input of a decade counter chip 41. The drop 33 passing the drop detector probe 19 will increment the decade counter chip 41. If the count reaches 10 prior to the decade counter reset signal derived from the timer chip 42, a signal will become available at the microcomputer output. The timer chip 42 will automatically reset the decade counter chip 41 after a set time delay.

Referring to FIG. 8 and 5b, the overflow conditions are detected by the liquid detection chip 39 through the overflow detector probe 20. A zero to 15 second time delay is initiated by the time delay circuit 48. At the end of the time delay a pulse triggers the timer chip 42. The timer chip 42 will light the LED 44 and deliver an interrupt pulse to the microcomputer interface. The Schmidt trigger chip 43 is used for signal modifications because debouncing is not required for this circuit.

The illustrated flow cell can have many uses. The film established in the cell can be viewed spectroscopically and in other ways. It is possible to probe the film, take samples from the film, and add substances to the film. By placement and control of the applicators, it is possible to establish pulsations and standing waves in the film as a result of drops contacting the film. When an impinging drop contacts a flowing film, it can cause the film to oscillate for several cycles. These methods of use are helpful in certain specific analytical procedures.

For example, devices according to the present invention are useful in reaction rate studies. Droplets of liquid added from secondary applicators will give different measurement results, depending on the rate of liquid application, if they contain a rate-limiting reactant. Thus, if two runs are made to apply liquid at different rates, e.g. by using different diameter applicator tubes, it is possible to detect responses of different intensities if a rate limiting reactant is present in the applied liquid. A comparison of the intensity of the responses and the volumes of applied liquid would also provide information on the rate of reaction.

In the illustrated embodiment, the falling film that is formed is a classic example of a laminar flow region. The diffusion-controlled mixing in a laminar flow region can be enhanced by additional mass transfer processes, establishing a temperature gradient, initiating a rapid chemical reaction, or by mechanical agitation. For the falling-film flow cell, mixing occurs by inducing a mechanical agitation of the falling-liquid film with an intersecting reagent stream from an applicator. This film agitation is the result of rapid pulsations that are produced by the periodic necking of a reagent solution in a gap between the reagent applicator and falling film. This gap or tube-to-film spacing is the critical parameter for obtaining good mixing characteristics.

At the two air-to-liquid interfaces of the film, the film pulsations resulting from the necking appear as periodic swells with a frequency and an amplitude minimum and maximum that define the envelop encompassing both interfaces. Once formed, the amplitude of each pulse is dampened downstream by the loss of energy to the falling film. Thus, the agitation of the film decreases downstream to a degree that the mixing of reagents probably becomes negligible by the third or fourth oscillation.

The frequency of the film pulsations is empirically adjusted by first butting the reagent applicator tube against a previously established falling film. Next, the reagent tube is withdrawn slowly to a position corresponding to a visible turbulence on the film that is discerned by a loss of transparency. The film turbulence and presumably the mixing efficiency increase as the tube is withdrawn slowly to a position corresponding to a visible turbulence on the film that is discerned by a loss of transparency. The film turbulence and presumably the mixing efficiency increase as the tube is withdrawn still further until a gap size is reached where the fluid first breaks contact with the falling film. This withdraw of the reagent tube causes the solution exiting the tube to project beyond the boundaries of the tube leading to a low velocity jet flow. Fluid flow with free boundaries from an orifice, or in this case a reagent applicator tube, is defined as a jet flow. The jet breaks up at a point that is dependent on turbulence in the jet, interfacial tension, density, and viscosity of the fluids. The optimal spacing or gap distance is proportional to the critical length of necking. The critical length for necking of a low velocity jet is believed to be equivalent to a dimension described by the circumference of the tube.

A hypothesis on the cycle that leads to necking is graphically illustrated by the sequence of events that is depicted as stages a through e in FIG. 14. In this example, the applicator 55b is a Teflon tube with a 0.70-mm i.d. Secondary injector fluid 80 is delivered to the film 31. Prior to making contact with the film 31, fluid 80 projected from the applicator 55b occupies a spherical volume 82 of about 4.1 $\mu$L. The B-factor for stages a-e is 0.9. For stage f the B-factor is 1.1. Dead time for stages a-b is 0.14 s. The cycle begins and ends at stage a where the meniscus in the reagent tube has returned to its equilibrium position where there are no pressure imbalances at the liquid-to-air interface and the previous droplet has merged downstream with the falling film Stage b shows the cross-section of a spherical droplet that has formed in the gap between the tube and falling film. Since the reagent stream from the tube is isolated from the film, the flow rate and linear velocity are at a minimum. Stages c-e illustrate that portion of the cycle that leads to the mixing of two reagents. If the two intersecting reagents initiate a fast CL reaction, then a CL signal may be detected during this time. The meniscus depicted in stage 3 is in a retracted position due to a snap back of the thread of fluid following droplet break-off. Also, the flow rate and linear velocity are at a maximum since the droplet and film have merged. The meniscus is envisioned to oscillate between this retracted position and a projected position for a very short time prior to returning to the normal or equilibrated position shown in stage a. Stage f illustrates the formulation of a droplet that will eventually fall from the tube without making contact with the film. This condition is caused by a tube-to-film gap that is too large.

The proper spacing that leads to efficient mixing can be estimated by first determining the critical period or pulse length to achieve necking. The pulse length, $I_p$, for the initialization of necking in a flowing reagent stream can be estimated from equation (1).

$$I_p \approx 2\pi r \quad (1)$$

where r is equal to the internal radius of the reagent applicator tube. For non-wetting materials, the inside diameter is used. For materials that wet the outside diameter is used. The cutting of the Teflon tube tip is typically done at a right angle; however, some solutions required a conical tip to assure the limiting diameter is the inside diameter.

The tube-to-film spacing distance, $I_s$, is equivalent to the product of the spacing factor, B, and $I_p$ as shown by equation (2).

$$I_s \approx B \times I_p \quad (2)$$

The spacing factor has no units, can be empirically derived, and is always less than or equal to one to prevent the formation of droplets. An optimal spacing distance is influenced by the surface tension of the solution in the secondary reagent port and the diameter of the secondary port tube when low flow rates are used. Ideally, the spacing factor should be as small as possible to minimize the resulting dead volume and dead time of the flow cell. The B-factor range that results in good mixing properties is 0.7 to 1.0.

The minimal dead volume and dead time associated with a flow cell are both important parameters if the flow cell is to be coupled to a separation scheme. The dead volume for the illustrated cell is defined as the fluid volume difference between the volume of a sphere that could just occupy the gap and a cylinder that extends across the gap with the same radius as the tube. The dead time is the time required to fill the gap between the tube and film by a flowing stream. The dead volume $V_d$, and dead time, $t_d$, can be estimated from equations (3) and (4), respectively, where F is the flow rate of the solution in the reagent tube.

$$V_d \approx V_g - (2\pi r^2 I_s) \quad (3)$$

$$t_d \approx V_g/F \quad (4)$$

Therefore, the calculated dead volume and the dead time are 2.6 μL and 0.14 s, respectively, when the experimental conditions are as discussed above regarding FIG. 14. This is near the upper limit for maintaining resolution with microbore HPLC columns.

A new flow cell designed to use an HPLC effluent tube with a 130-μm bore diameter, a flow rate of 0.01 mL/min and a B factor of 0.8 would have a calculated dead volume of 10 nL and a dead time of 0.11 s. Although the design constraints of adjusting a 0.3-mm tube-to-film spacing for such a cell could probably be met, the problems associated with designing a microflow cell that could operate with these low flow rates are unknown.

If one desires to avoid or reduce the oscilations which result from the addition of liquid from a secondary applicator, two applicators can be positioned to face one another on opposite sides of the film. A number of different measurement effects can be achieved by adjusting the flow rates of such opposed applicators relative to each other.

When operating in a static film mode, a film is established by initial flow from an applicator, but liquid is not drained or otherwise removed from the film. Static films are typically short lived. But, a static film can be preserved for a substantial period by maintaining the film in a chamber that contains an atmosphere that is substantialy saturated with the liquid which comprises the film.

Referring now to FIGS. 9, 10, 11 and 12, a microvolume mixing chamber is shown. A plurality of reagents are transported to the film supports to form a film by means of a plurality of reagent ports 72 and 73. Downstream from said ports the homogenous mixture of reagents may then be transferred to other locations by pump or gravity flow. The hollow cylinder 76 could be enclosed by top window 62, bottom window 63, side window 64, and front window 65. Through the use of pressure regulating gas inlet/outlet 71, the environment of the hollow cylinder 76 may be controlled with respect to pressure and type. Additionally, the type of environment may be reactive or passive similar to the film supports 5.

Referring to FIG. 13, it is readily apparent the film will flow down the film supports 5 and be directed to the geometrically-shaped nodes 84 at which point additional mixing of the reagents should occur prior to the formation of film below the geometrically-shaped node 84 or mixing aid. The design of the nodes and the number of nodes placed in line would affect the mixing efficiency.

There are other methods for withdrawing a flowing film from a flow cell or micro-volume mixing chamber. Use of a drain cavity may not be suitable, particularly if liquid in the film must be collected for subsequent analysis at detecting or fraction collecting instrumentation. A collection tube, similar to the illustrated wettable reagent tubes, can be butted against the falling film 31 and the film support 5 at an angle through a reagent port, for example, 55a. Similarly, in the micro-volume mixing chamber, a wettable collection tube can be placed through a reagent port, for example, port 73. Plug flow through the collection tube can be obtained by gravity, if the collection tube is located at the bottom of a downwardly flowing film, or by applying suction to the collection tube.

The illustrated film supports are parallel wires, but the supports could be any bodies that provide opposed, extended edges between which a film can be formed. Knife blades could be used in place of the illustrated wires, the taper of the blades being selected to provide edges which favor film formation. Portions of the blades, other than the edges, can be coated with or made of a nonwetting substance so that liquid is not wicked away from the edges. In particular, a Teflon coating can be provided on portions of the blades away from the edges.

The film support edges need not extend parallel to each other, although a parallel arrangement will be necessary for certain procedures. Nor is it necessary that the edges be static. The edges could comprise films of mercury flowing down along the surfaces of underlying support bodies.

While the particular invention herein shown and described in detail in two preferred embodiments, it is to be understood that they are merely illustrative of the presently preferred embodiments of the invention and that no limitations are intended to the details of construction or design shown other than as defined in the appended claims, which form a part of this disclosure.

We claim:

1. A method of forming a flowing film, wherein the film flows from an upstream position adjacent a primary applicator through a film forming chamber to a downstream position adjacent a drain port of said chamber, said method comprising, in order:

providing two elongated, opposed film supports spaced from a sidewall defining said chamber and spaced from each other to define a gap therebetween along opposed extended longitudinal edges thereof;

applying a vacuum to a drain port located adjacent to the gap;

initiating a feeding of a first liquid to the gap through a secondary applicator which is positioned adjacent to the gap at a distance from the drain port so that the liquid is supported as a film between the edges of the supports and flows along both edges toward the drain port; and initiating a feeding of a second liquid that may be the same as or different from the first liquid to the gap through a primary applicator which is positioned adjacent to the gap at a location that is farther distant from the drain port than is the secondary applicator, the second liquid from the primary applicator establishing a film which flows between the supports toward the drain port and to which film is added liquid from the secondary applicator.

2. The method of claim 1 wherein the film supports comprise active film supports.

3. The method of claim 1 wherein the film supports comprise passive film supports.

4. The method of claim 1 wherein the film supports are cell wires, each cell wire having a top and a bottom, the bottom being adjacent the drain port.

5. The method of claim 4 additionally comprising adjusting at least one of the feedings by changing the position of at least one of the applicators with respect to the cell wires.

6. The method of claim 4 further comprising the step of transmitting a warning signal when an overflow occurs near the bottom of the cell wires.

7. The method of claim 1 further comprising the step of initiating the feeding of a liquid to the gap through a tertiary applicator which is positioned adjacent to the gap at a location between the drain port and the secondary applicator.

8. A method of rapidly mixing multiple reagents in a film forming chamber, the method comprising:

providing two elongated, opposed film supports spaced from a sidewall defining said chamber and spaced from each other to define a gap therebetween along opposed extended longitudinal edges thereof, each edge having an upstream end and a downstream end;

feeding a first liquid to the gap through a primary applicator which is positioned adjacent to the gap such that the feeding of the first liquid from the primary applicator provides a laminar flow film which is supported between the edges flows as a stream along both edges toward the downstream end of both edges; and feeding a second liquid to the gap through a secondary applicator which is positioned adjacent to the gap at such a location that a jet stream of the second liquid intercepts and combines with the laminar flow film.

9. A method of forming a flowing film, wherein the film flows from an upstream position adjacent a primary applicator through a film forming chamber to a downstream position adjacent a drain port of said chamber, comprising, in order:

providing two elongated, opposed cell wires spaced from a sidewall defining said chamber, the cell wires defining a gap therebetween along opposed longitudinal edges thereof, the cell wires being supported on a frame comprising (a) an upper body plate defining cell holes which extend from a bottom of a upper body plate to a top of the upper body plate and into which the cell wires extend, and (b) a lower body plate defining cell holes which extend from a top of the lower body plate to a bottom of the lower body plate and into which the cell wires extend;

applying a vacuum to a drain port located adjacent to the gap;

initiating a feeding of a first liquid to the gap through a secondary applicator which is positioned adjacent to the gap at a distance from the drain port so that the liquid flows as a film between the cell wires toward the drain port; and initiating a feeding of a second liquid that may be the same as or different from the first liquid to the gap through a primary applicator which is positioned adjacent to the gap at a location that is farther distant from the drain port than is the secondary applicator, the second liquid from the primary applicator establishing a film which flows between the cell wires toward the drain port and to which film is added liquid from the secondary applicator.

10. The method of claim 9 further comprising the step of supporting the cell wires including:

an upper wire spacer attached to the bottom of the upper body plate where the upper wire spacer defines an opening within which project upper wire spacer prongs positioning the cell wires; and a lower wire spacer frictionally held within a lower body plate where the lower wire spacer defines a clearance hole positioning each of the cell wires.

11. The method of claim 9 wherein the step of initiating the feeding through a primary applicator is accomplished by passing the second liquid through a passageway which extends through the upper body plate and terminates directly above the cell wires.

12. The method of claim 9 further comprising the step of withdrawing the liquid film from the gap through the drain port.

13. The method of claim 12 wherein the step of withdrawing the liquid film comprises:

drawing air through an air inlet port into an air inlet cavity through which the cell wires extend; and drawing the air and the liquid film from the air inlet cavity through clearance holes defined through a lower wire spacer, to a drain cavity which communicates with the drain port.

14. The method of claim 13 wherein the step of withdrawing the liquid film further comprises the step of withdrawing the liquid through at least one wettable reagent tube positioned to receive the flowing film.

* * * * *